US 6,565,573 B1

(12) United States Patent
Ferrante et al.

(10) Patent No.: US 6,565,573 B1
(45) Date of Patent: May 20, 2003

(54) ORTHOPEDIC SCREW AND METHOD OF USE

(75) Inventors: Joseph Ferrante, Barlett, TN (US); Angie Black, Mason, TN (US)

(73) Assignee: Smith & Nephew, Inc., Memphis, TN (US)

( * ) Notice: Subject to any disclaimer, the term of this patent is extended or adjusted under 35 U.S.C. 154(b) by 81 days.

(21) Appl. No.: 09/836,811

(22) Filed: Apr. 16, 2001

(51) Int. Cl.$^7$ ............................................. A61B 17/56
(52) U.S. Cl. ........................................................ 606/73
(58) Field of Search ............................ 606/72, 73, 104, 606/64, 70, 71, 60

(56) References Cited

U.S. PATENT DOCUMENTS

| | | | |
|---|---|---|---|
| 1,007,107 A | | 10/1911 | Hulsmann |
| 4,319,420 A | | 3/1982 | Clinton |
| 4,429,600 A | | 2/1984 | Gulistan |
| 5,139,499 A | | 8/1992 | Small et al. |
| 5,246,441 A | | 9/1993 | Ross et al. |
| 5,259,398 A | | 11/1993 | Vrespa |
| 5,456,685 A | * | 10/1995 | Huebner ............... 411/311 |
| 5,591,166 A | * | 1/1997 | Bernhardt et al. ........... 606/60 |
| 5,697,929 A | | 12/1997 | Mellinger |
| 5,797,914 A | | 8/1998 | Leibinger |
| 5,925,048 A | * | 7/1999 | Ahmad et al. ............... 606/73 |
| 5,951,560 A | | 9/1999 | Simon et al. |
| 5,964,768 A | | 10/1999 | Huebner |
| 6,030,162 A | * | 2/2000 | Huebner ............... 411/263 |
| 6,306,140 B1 | * | 10/2001 | Siddiqui ............... 606/72 |
| 6,322,562 B1 | * | 11/2001 | Wolter ............... 606/60 |
| 6,355,043 B1 | * | 3/2002 | Adam ............... 606/62 |

FOREIGN PATENT DOCUMENTS

| | | |
|---|---|---|
| DE | 298 09 736 U1 | 1/1999 |
| DE | 198 52 945 A1 | 5/2000 |
| EP | 0 387 392 A2 | 9/1990 |
| FR | 2 704 170 | 10/1994 |

OTHER PUBLICATIONS

U.S. patent application Ser. No. 09/226,229, Pepper, filed Jan. 7, 1999.
Brochure entitled "Cannulated Hip Pin", General Operative Techniques as described by John P. Lydent, M.D. (undated).
Brochure entitled "Compression Hip Screw Plates and Nails Surgical Technique" (undated).
Smith & Nephew Richards Orthopaedic Catalog, pp. G–15, H–4, I–5, I–13, T–5 (undated).
Synthes, The Self–Drilling Schanz Screw Technique Guide, GP 0468–A, 11/95 (undated).
Brochure entitled Russell–Taylor Reconstruction Nail System Universal Instrumentation (undated).
Photo of Smith & Nephew, Inc. instrument: fixed handle (undated).
Photo of Smith & Nephew, Inc. instrument: driver set (undated).
Photo of Smith & Nephew, Inc. instrument: driver exploded view (undated).
Synthes, page entitled "Instruments to Lock Proximally" (undated).

(List continued on next page.)

Primary Examiner—Eduardo C. Robert
(74) Attorney, Agent, or Firm—Kilpatrick Stockton LLP

(57) ABSTRACT

This invention is directed to an orthopedic screw with a screw head, a screw body with distal tip, a shank with an enlarged diameter at the trailing end and a thread extending radially outward from the shank, and an internal capture surface. This invention also provides a system for use in an orthopedic surgical procedure including the screw, an orthopedic implant adapted to be secured in a patient with the screw, and a driver capable of engaging the internal capture of the screw. The invention further provides methods of using the screw, the system, and the screw and driver assembly.

24 Claims, 10 Drawing Sheets

OTHER PUBLICATIONS

Photo of 3 separate pieces to do the functions of hand and power (Smith & Nephew) Apr. 29, 1998.

Photo of integral handle and shank for power (Smith & Nephew) Apr. 29, 1998.

Photo of dual mode driver exploded view (Smith & Nephew) Apr. 29, 1998.

Photo of loaded screw with thread in head (Smith & Nephew) Apr. 29, 1998.

Photo of screw connected to power (Smith & Nephew) Apr. 29, 1998.

Photo of screw drilling into bone (Smith & Nephew) Apr. 29, 1998.

Photo of screw removed from power (Smith & Nephew) Apr. 29, 1998.

Photo of screw with release handle from power position by moving collar (Smith & Nephew) Apr. 29, 1998.

Photo of rotating handle to hand position (Smith & Nephew) Apr. 29, 1998.

Photo of in hand driver mode (Smith & Nephew) Apr. 29, 1998.

Photo of driving by hand (Smith & Nephew) Apr. 29, 1998.

Photo of withdrawing lock bar (Smith & Nephew) Apr. 29, 1998.

International Search Report in related PCT/US02/11038 dated Jul. 25, 2002.

* cited by examiner

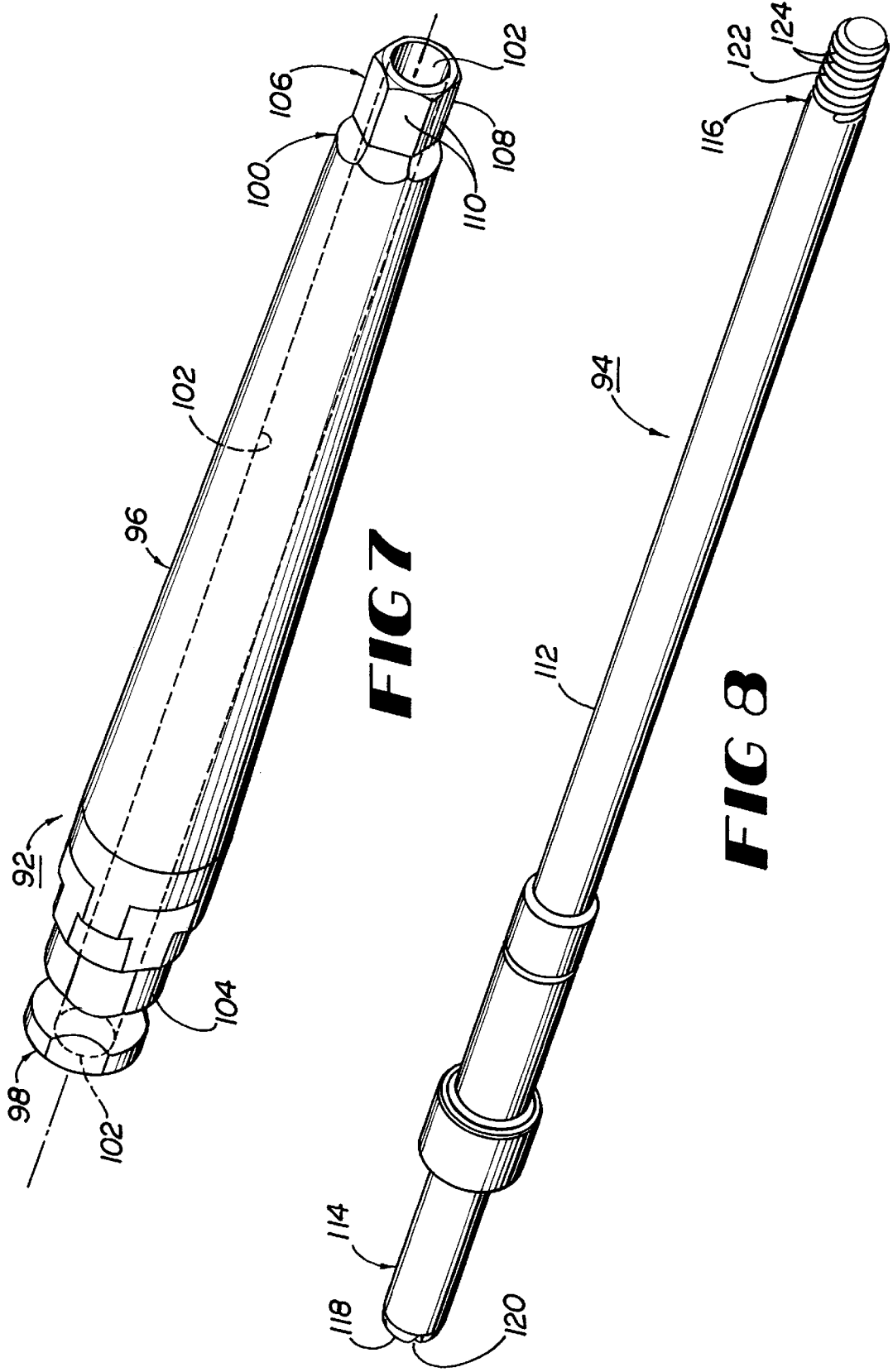

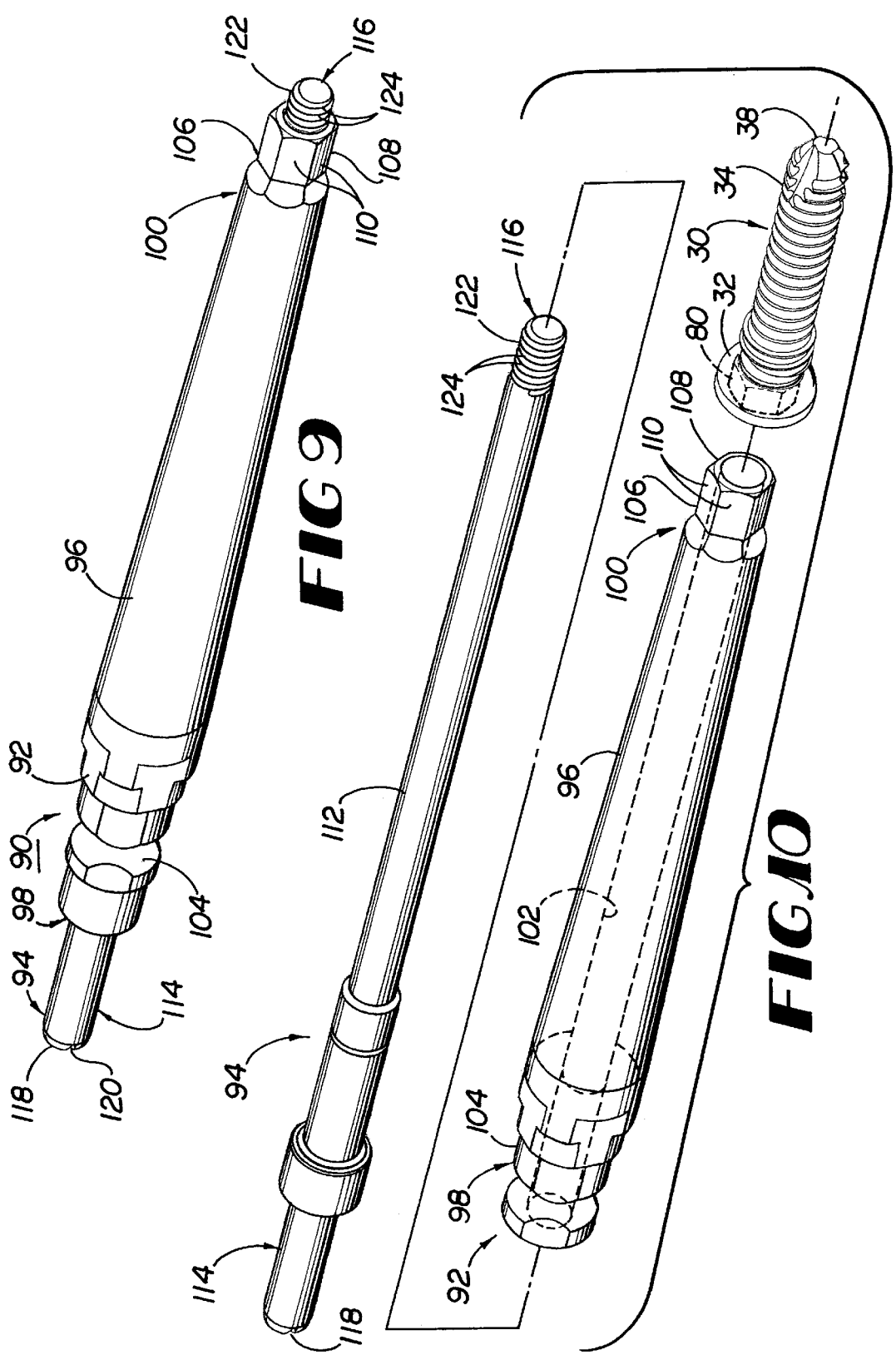

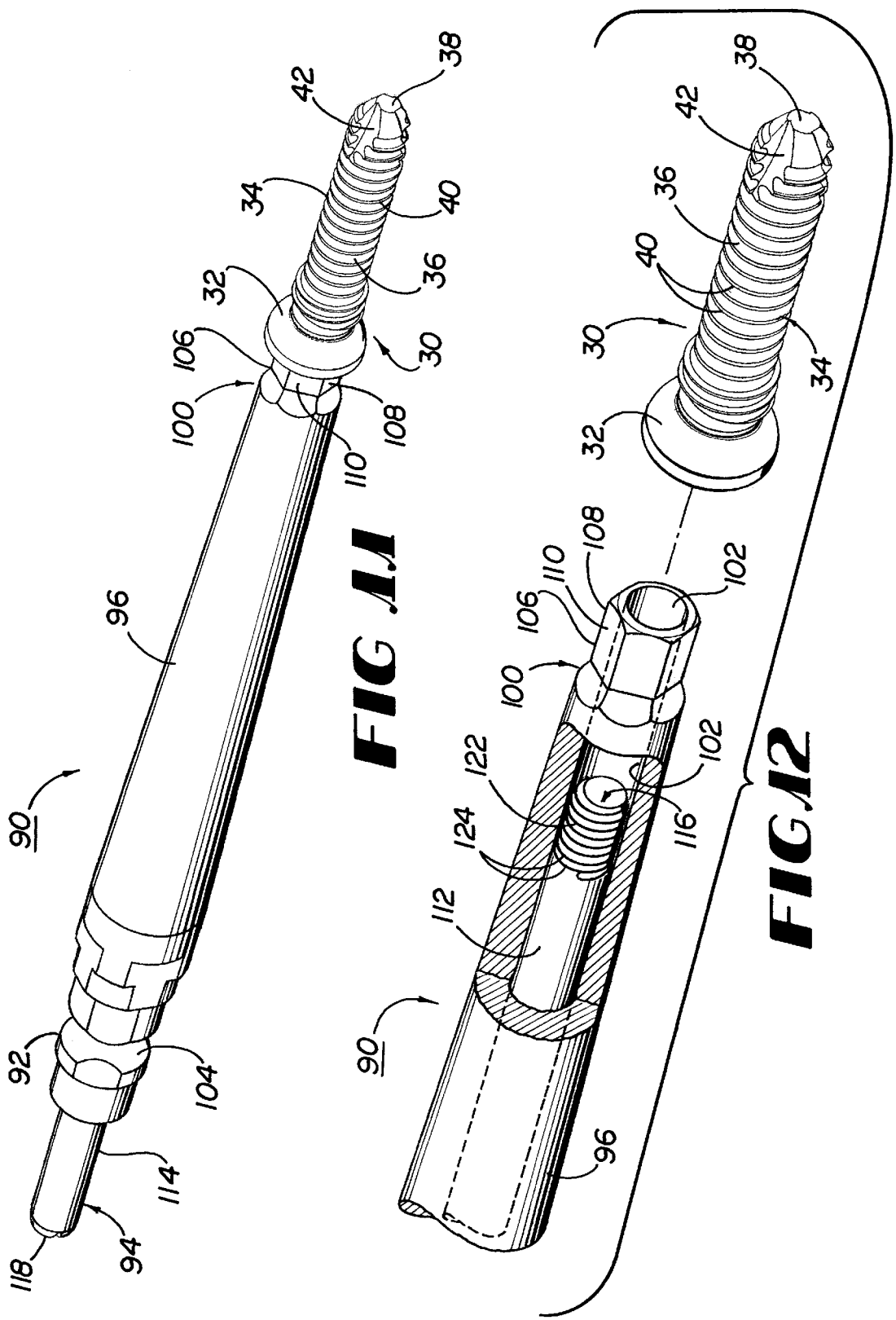

ORTHOPEDIC SCREW AND METHOD OF USE

FIELD OF THE INVENTION

This invention relates generally to methods, instrumentation and devices for use in a surgical procedure for the repair of bone fractures and the fixation of orthopedic implants. More particularly, this invention relates to methods, instrumentation and devices for securing an orthopedic implant, such as a bone fracture reduction rod, intramedullary nail, or other prosthetic device. This invention even more particularly relates to an improved orthopedic screw with an enlarged shank diameter at the trailing end of the screw and an internal capture surface recessed into the head and at least part of the trailing end, along with a driver capable of engaging the internal capture of the screw.

BACKGROUND OF THE INVENTION

Surgeons perform a variety of orthopedic procedures requiring screws specifically designed for use in bone tissue. A wide array of bone screws exist which are adapted to perform specific functions or to be compatible with a specific type of bone tissue or orthopedic implant.

For example, in order to stay a bone fracture, particularly in a long bone, a surgeon may insert a bone fracture reduction rod, or intramedullary nail, into an intramedullary canal of the bone. In order to secure the rod, the surgeon will place bone screws through holes in the intramedullary nails. Screws used for this purpose often extend through the bone and the hole in the nail and into the far cortex on the opposite side of the long bone. The use of such screws provides many advantages such as increasing the rotational stability of the implanted nail, enhancing the union rate of the bone, and promoting limb rehabilitation.

However, the use of such bone screws also presents certain challenges. For example, a surgeon often needs to have several drivers available during a procedure because a single nailing system typically employs a large number of different screws of various sizes. As a result, the surgeon may be required to exchange drivers in the middle of the procedure. Moreover, bone screws which are not secured to the driver during implantation can slip off and become lost within surrounding muscle tissue. Retrieval of these screws proves difficult when the bone area is surrounded by a large amount of soft tissue, such as in the areas adjacent the forearm and the proximal thigh, particularly in larger patients. The delay in retrieving the lost screw and other inconveniences and risks associated with the loss of screws during surgery are not only unnecessary, but can compromise the success of the procedure.

Therefore, in performing orthopedic surgery it is desirable for the bone screw to be coupled to a driver to allow attachment of the screw to the driver prior to implantation in the bone, in order to avoid losing the screw in the surrounding soft tissue during the procedure, and to allow release of the screw in a desired manner after implantation. Screw and driver combinations exist which allow axial attachment of the screw to a driver prior to insertion, after which the surgeon rotates the driver until the screw is fully implanted. After implantation, the driver is disengaged from the screw. However, although known screw and driver combinations help reduce the risk of screw loss, these previous capture mechanisms typically suffer from one or more problems which limit their utility and performance.

For instance, prior art screw and driver combinations exist which utilize an external capture mechanism, such as a geometrically shaped head for engaging a driver with a socket for receiving the shaped head. However, these mechanisms proved undesirable due to irritation of the surrounding soft tissue caused by the bulky heads. Additionally, often a surgeon desires to countersink the head of the screw into the bone so that the top of the head is flush with or beneath the bone surface to further avoid tissue irritation, but the heads of the external capture screws can not be appropriately countersunk. Other external capture mechanisms include drivers with chalk-holder type devices for grasping the head of the screw during implantation. Screws with smooth, rounded heads, which cause less tissue irritation, can be used with such drivers; however, the use of a chalk-holder type mechanism does not allow for a tight seating of the head against the bone and also prevents countersinking of the screw head within the bone.

Prior art screw and driver combinations also exist which possess internal driving mechanisms, such as an internal hex socket for receiving a corresponding driver. However, these screws merely allow for proper seating and countersinking of the screw head or top end of headless screws, but do not provide an internal capture surface for securing the screw to the driver prior to insertion in the bone in a manner that allows the screw to stay positioned on the driver during manipulation, yet be released when desired.

Some such screws additionally include an axial cannulation through the length of the screw body through which a guide wire is threaded to both guide the screw to the insertion sight and allow retrieval of the screw if lost prior to or during insertion, such as screws with an internal driving surface and a cannulated design. The guide wire method allows for re-capture of a lost screw but does not prevent the initial loss of the screw due to disengagement from the driver during insertion.

Prior art screw and driver combinations which provide for internal capture of the screw prior to insertion often do not allow sufficiently rigid capture of the screw to the driver to prevent movement of the screw relative to the driver during insertion, and such screws frequently possess other serious structural and functional problems. For instance, prior art screws having one or both of an internal capture surface and internal driving surface are disadvantageous in that the creation of the socket, enlarged bore, or other recession into the head and upper portion of the screw shank reduces the structural soundness and weakens the fatigue strength of the screw, which may result in breaking of the head or upper portion of the shank.

Accordingly, what is needed is an orthopedic screw with an internal capture surface capable of rigidly engaging a driver prior to and during insertion of the screw in a patient yet releasing from the driver when desired, while simultaneously maintaining structural soundness and adequate fatigue and head break strength. Also needed is a driver designed to correspond to the internal capture and driving mechanism of the screw, and methods of implanting and using the screw. Further, what is needed is a system for use in a procedure for the fixation of an orthopedic implant in a patient that includes an orthopedic implant and screws with an internal capture surface and adequate strength which are adapted to secure the implant to the skeletal system of a patient.

SUMMARY OF THE INVENTION

Methods, devices and instrumentation of this invention seek to provide an orthopedic retaining device capable of being rigidly coupled to an insertion tool while maintaining structural and functional integrity of the retaining device and capable of being released from the insertion tool after insertion. Rigid internal capture is possible without compromising the strength of the retaining device and while avoiding irritation to surrounding tissue.

Methods, devices and instrumentation according to this invention more particularly provide an orthopedic screw, an orthopedic screw and driver assembly, a system employing the orthopedic screw for the fixation of orthopedic implants, and methods of using the screw, assembly, and system that provide adequate capture of an orthopedic screw to avoid loss of the screw during implantation, while also maintaining adequate structural and functional integrity of the screw. These and other aspects of the orthopedic screw, assembly, and system of this invention make them easier and more practical to use than prior art orthopedic screws, assemblies, and systems.

One orthopedic screw according to this invention includes a head, an internal capture surface, and a shank extending from the screw head to a distal tip. The screw shank has an enlarged diameter at the trailing end, in the area just under the head of the screw, in order to accommodate the internal capture surface without sacrificing the strength or structural soundness of the screw. The screw also includes a continuous thread along at least a portion of the shank extending radially outward from the shank. The enlarged diameter of the trailing end of the shank of a screw according to this invention provides adequate strength and better purchase of the bone material.

The internal capture surface of the screw allows the screw to be securely attached to a driver prior to insertion of the screw into the bone and released from the driver after insertion, which avoids the loss of the screw in the soft tissue of the patient during the procedure. The enlarged diameter of the trailing end provides structural reinforcement in the area of the shank below the head in order to compensate for strength lost due to the recession of the capture mechanism into the head and upper body of the screw.

One screw assembly according to this invention includes an orthopedic screw, as described above, in combination with a driver having a driving member adapted to engage the internal capture surface of the screw, and a locking member adapted to engage the internal capture surface of the screw to secure the screw to the driver.

An additional aspect of this invention is an system for use in fixing an orthopedic implant in a patient. Such a system includes screws of this invention and an orthopedic implant, such as an intramedullary nail or fracture reduction rod, an orthopedic plate, external fixture, tibia base, or acetabular shell, which can be secured to the skeletal system of a patient using an orthopedic screw according to this invention.

Another aspect of this invention also seeks to provide a method of using the orthopedic screw assembly for manipulating a screw in bone material without a significant risk of losing the screw. Another aspect of this invention provides a method of using the orthopedic screw and screw assembly for repairing a bone fracture or for fixing an orthopedic implant in a patient.

The screws and screw assemblies of the present invention provide many benefits and advantages. One feature according to one aspect of this invention is the ability to safely drill a bone screw with a variety of drivers including power and hand drivers.

Another feature of another aspect of this invention is a bone screw that will not cause significant irritation to adjacent soft tissue and that is adapted for countersinking into the bone.

Another feature of an aspect of this invention is a bone screw with an internal capture surface without a corresponding reduction in screw strength or integrity. The screw is structurally sound and is at least equivalent in strength to bone screws without internal capture surfaces which are currently on the market.

Yet another feature of an aspect of this invention is an orthopedic screw assembly that securely retains a screw to a driver prior to and during insertion of the screw into a bone to avoid loss of the screw in surrounding soft tissue.

Another feature of an aspect of this invention is the ability to easily release the screw from the driver after insertion into the patient.

These and other features of this invention will become apparent after a review of the following detailed description of the disclosed embodiments.

BRIEF DESCRIPTION OF THE DRAWINGS

FIG. 7 is a side view of the sleeve portion of a driver according to one embodiment of this invention.

FIG. 8 is a side view of a locking member of a driver according to one embodiment of this invention.

FIG. 9 is a side view of a driver according to one embodiment of this invention showing the locking member of FIG. 8 inserted into the sleeve member of FIG. 7.

FIG. 10 is an exploded perspective view of a screw assembly according to one embodiment of this invention.

FIG. 11 is a perspective view of a screw assembly according to one embodiment of this invention.

FIG. 12 is a side view in partial cross-section of a screw assembly according to one embodiment of this invention.

DETAILED DESCRIPTION

Figure 1:
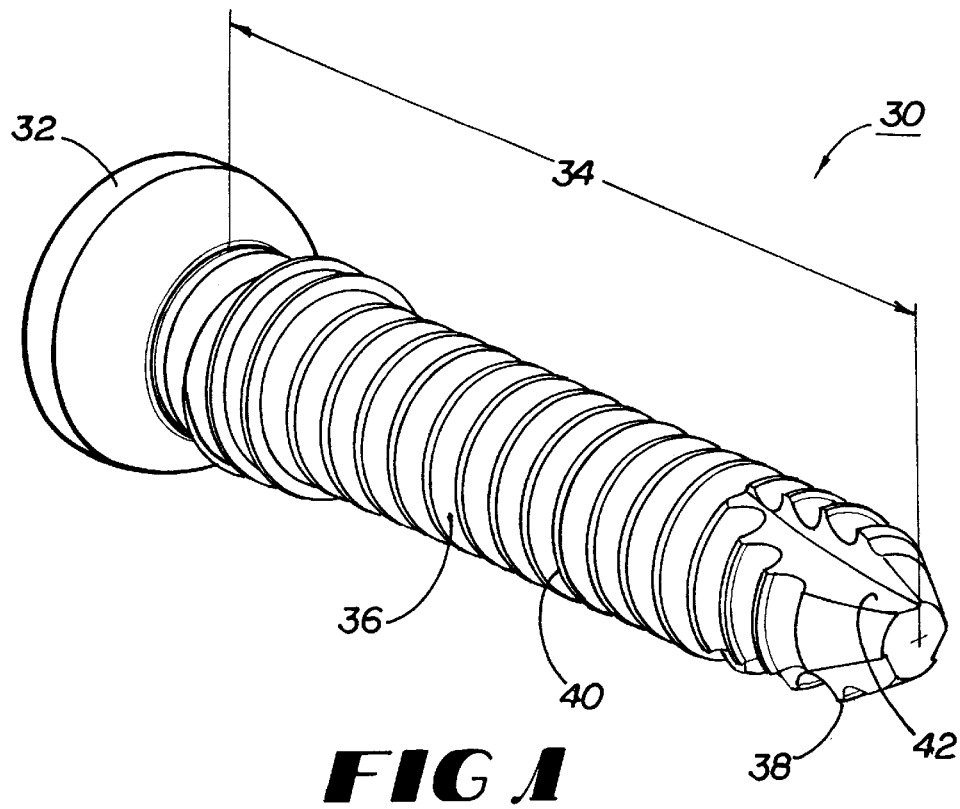
FIG. 1 is a perspective view of a bone screw according to one embodiment of this invention.
Figure 2:
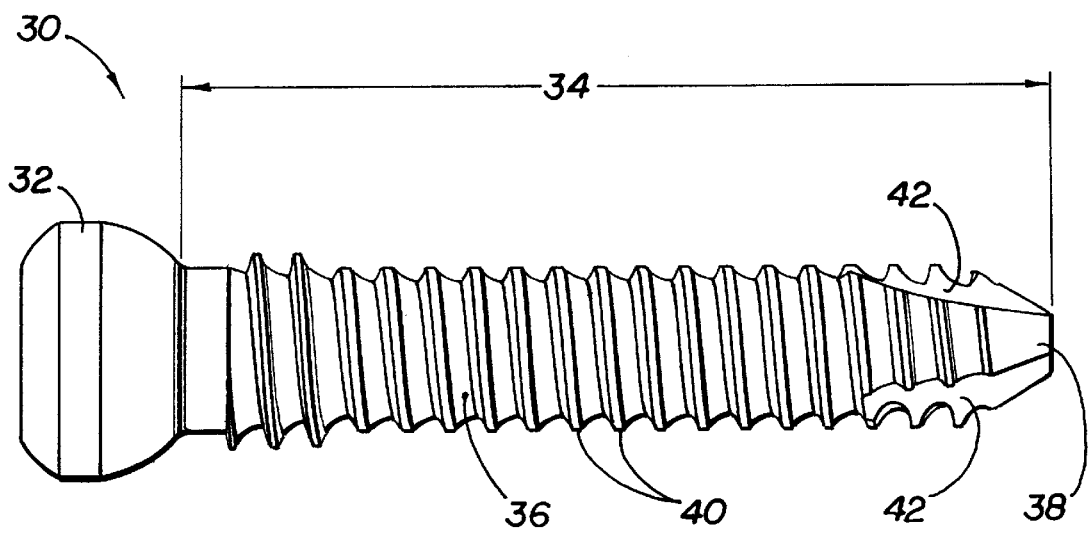
FIG. 2 is a side view of the screw of FIG. 1.
Figure 3:
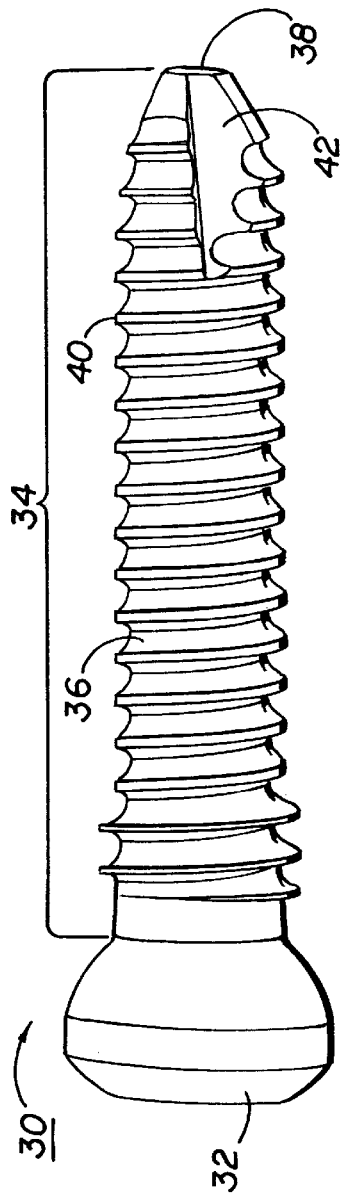
FIG. 3 is a top plan view of the screw of FIG. 1.

Methods, devices and instrumentation according to this invention seek to improve orthopedic surgical procedures involving the use of orthopedic screws, such as placing screws in the fracture reduction of bones to stabilize a bone fracture and in fixing orthopedic implants to the skeletal system of a patient. Methods, devices and instrumentation according to this invention provide an orthopedic screw having an internal capture surface and an enlarged diameter at the trailing end of the shank. Internal capture allows a countersink of the screw, thereby minimizing irritation to surrounding tissue. The enlarged shank diameter at the trailing end provides structural reinforcement to the area of the screw housing the internal capture surface and also allows better purchase of the bone material.

Methods, devices and instrumentation according to this invention seek to provide a screw assembly including an orthopedic screw and driver with driving and retaining members for simultaneously driving the screw into the bone while securing the screw to the driver to avoid loss of the screw during insertion. The screw, screw assembly, and methods of use improve orthopedic surgery by reducing the risk of losing the screw during the surgical procedure and by providing this advantage without a corresponding loss of screw strength, stability, fit or comfort.

Consider one example of the instrumentation and devices according to this invention. Generally, an orthopedic screw of this invention includes a head or top end, an internal capture surface, and a shank extending from the screw head to a distal tip. As used herein the term "head" means any head or top end of a screw which houses at least a portion of an internal capture surface. The screw shank has trailing end adjacent to the head of the screw, an intermediate section, and a leading end adjacent to the distal tip. The screw also includes a substantially continuous thread along at least a portion of the shank which extends radically outward from the shank. Preferably, the head of the screw is adapted for countersinking into the bone, and contains an internal capture surface recessed into the head and upper portion of the screw shank, which is adapted to engage and secure the screw to a corresponding driver in a manner that allows the screw to stay securely positioned on the driver during manipulation of the screw, yet be released from the driver when desired. To accommodate this recessed internal capture surface and provide adequate strength and structural reinforcement to the trailing end of the shank, the diameter of the shank is larger at the trailing end of the shank than in an adjacent shank section.

The screw assembly of this invention includes the orthopedic screw described above and a driver adapted to retain and engage the screw. The assembly may be manipulated by a surgeon to place the screw into a pre-drilled hole in a patient's bone and to drive the screw securely into the bone material. However, if the screw is a self drilling screw, a pre-drilled hold is not necessary. The surgeon may optionally countersink the head of the screw into the bone material to further avoid irritation of the surrounding tissue. Once securely seated in the bone, the surgeon can then release the screw by disengaging the driver from the internal capture surface of the screw.

The screw of this invention is adapted to be used alone or in conjunction with a system for use in repairing a bone fracture or in fixing an orthopedic implant in a patient. The screw can be used alone to aid in the reduction of small bone fractures. Additionally, a screw according to this invention can be used in conjunction with an orthopedic implant to fix the implant securely to the skeletal system of the patient. Possible orthopedic implants include, but are not limited to intramedullary nails or reduction rods, plates, external fixtures, tibia bases, and acetabular shells.

FIGS. 1 through 6 depict one embodiment of a screw according to this invention. As shown in the figures, orthopedic screw 30 includes a head 32 and a body 34. Preferably, head 32 is adapted to countersink into the bone in order to avoid soft tissue irritation by the head 32 of the screw 30. Body 34 includes shank portion 36 extending from head 32 to a tip 38 and a continuously advancing spiral ridge or thread 40 threaded evenly about the outer surface of the shank portion 36. Body 34 optionally also includes a flute 42 for the removal of bone chips as screw 30 is implanted into the bone. Tip 38 of body 34 is a self tapping, non-self drilling tip with a generally conical configuration with a foreshortened end, e.g. a frusto-conical tip.

Preferably, screw 30 is a self-tapping, non self-drilling bone screw so that tip 38 requires a predrilled hole before insertion into the bone and only thread 40 of screw 30 cuts into the bone. The pitch of the threading 40 at tip 38 should be sufficiently small to advance the screw 30 at a rate which allows tip 38 to advance into the bone, but sufficiently large to provide adequate bone purchase and to minimize the number of turns required to seat the screw. A suitable pitch for threading 40 may be in the range of about 5 threads-per-inch to about 50 threads-per-inch.

The length of the screw 30 should be adapted to correspond to the use of the screw. The screw can be any suitable length; preferably, the length of the screw 30 is generally from about 20 mm to about 160 mm. More preferably, the length of screw 30 is from about 20 mm to about 110 mm. Preferably, the length of the body is approximately 4 to 6 mm less than the total length of the screw, depending on the head shape and length.

Figure 4:
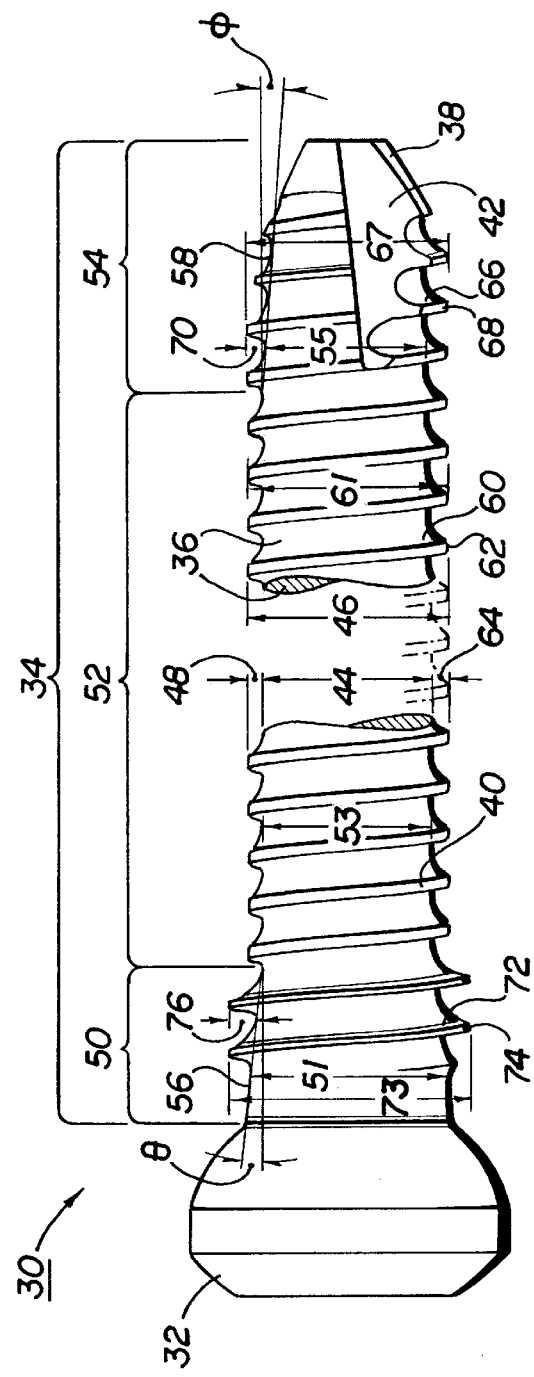
FIG. 4 is a partial side view of the screw of FIG. 1.

FIG. 4 is a side view of the screw of FIG. 1 and shows the detailed characteristics of the shank 36 and thread 40 of screw body 34. Screw body 34 has an minor diameter 44, defined by the diameter of the shank 36, and an major diameter 46, defined by the diameter of the thread 40. The thread height 48 is equal to one half of the difference between the minor diameter 44 and the major diameter 46. The difference is divided by two to account for the thread height on either side of the shank. Alternatively, major diameter 46 can be described as the sum of the minor diameter 44 and twice the thread height 48. Note that minor diameter 44, major diameter 46, and thread height 48 vary along the length of the screw body, as described below.

Shank 36 has three sections: trailing end 50; intermediate section 52; and leading end 54. Trailing end 50 is the portion of the shank adjacent to screw head 32, leading end 54 is the portion of the shank adjacent to the frusto-conical tip 38, and intermediate section 52 is the portion of the shank between the leading and trailing ends. Each shank section has a minor diameter 44 which may or may not remain constant from one section to another or within a section itself. Thus, trailing end 50 has a first minor diameter 51, intermediate section 52 has a second minor diameter 53, and leading end 54 has a third minor diameter 55.

Intermediate section 52, of the embodiment shown in FIGS. 1–6, has a generally cylindrical geometry with a substantially constant minor diameter 53. The minor diameter can be any suitable length adapted to the size and function of the screw. Preferably, the second minor diameter 53 of the screw of the present invention is generally from about 6.0 mm to about 3.5 mm, more preferably from about 5.5 mm to about 4.0 mm, and most preferably from about 5.0 mm to about 4.5 mm.

Trailing end 50 has a minor diameter 51 which is greater than second minor diameter 53 of the intermediate section. This enlarged minor diameter at the trailing end provides the ability to house at least part of an internal capture mechanism while maintaining sufficient fatigue and head break strength, qualities which are critical in this portion of the shank. This enlarged first minor diameter 51 may be provided by a taper of the trailing end, such that the taper widens from the intermediate section in the direction of the screw head.

In the embodiment shown in FIGS. 1–6, trailing end 50 includes first taper 56 extending between the intermediate section 52 and the screw head 30 at an angle θ. Although angle θ may be any suitable angle, θ is generally from about 1° to about 8°, and preferably from about 1° to about 3°. The tapered geometry of trailing end 50 is such that first minor diameter 51 increases from the section adjacent to intermediate section 52 in the direction of screw head 30. In this manner, first taper 56 provides the upper portion of the shank with an enlarged first diameter 51 towards the head of the screw to accommodate the recessed internal capture surface 78, shown in FIGS. 5 and 6, without sacrificing strength or structural integrity. Taper 56 also provides a wedge fit which allows the screw to feel tighter when seated in the bone.

In the embodiment shown, leading end 54 includes a second taper 58 extending from the end of the intermediate section 52 to the tip 38 at an angle φ. Angle φ may also be any suitable angle, and is generally from about 1° to about 8°, and preferably from about 1° to about 3°. Thus, leading end 54 has a generally tapered geometry such that the third minor diameter 55 decreases from the section adjacent to intermediate section 52 in the direction of tip 38. Second taper 58 narrows towards the tip of the screw creating a frusto-conical tip area, allowing the screw to follow the pre-drilled hole more effectively and to advance more easily into the bone and through an aperture in an orthopedic implant.

While the embodiment shown in FIGS. 1 through 4 has a taper at both the leading and trailing ends, any screw with an enlarged first minor diameter, to accommodate a recessed internal capture mechanism, is within the scope of this invention. For instance, a screw according to this invention may have a uniform taper along the shank such that the minor diameter continually decreases in the direction of the tip. Alternatively, a screw according to this invention may have a uniform minor diameter throughout the intermediate section and leading end such that the second and third minor diameters are equivalent.

Additionally, the screw thread, thread height, and major diameter of a screw of this invention may vary along the length of the screw body. As with the minor diameter, each shank section has a corresponding thread section and major diameter defined by the relative thread height.

Figure 5:
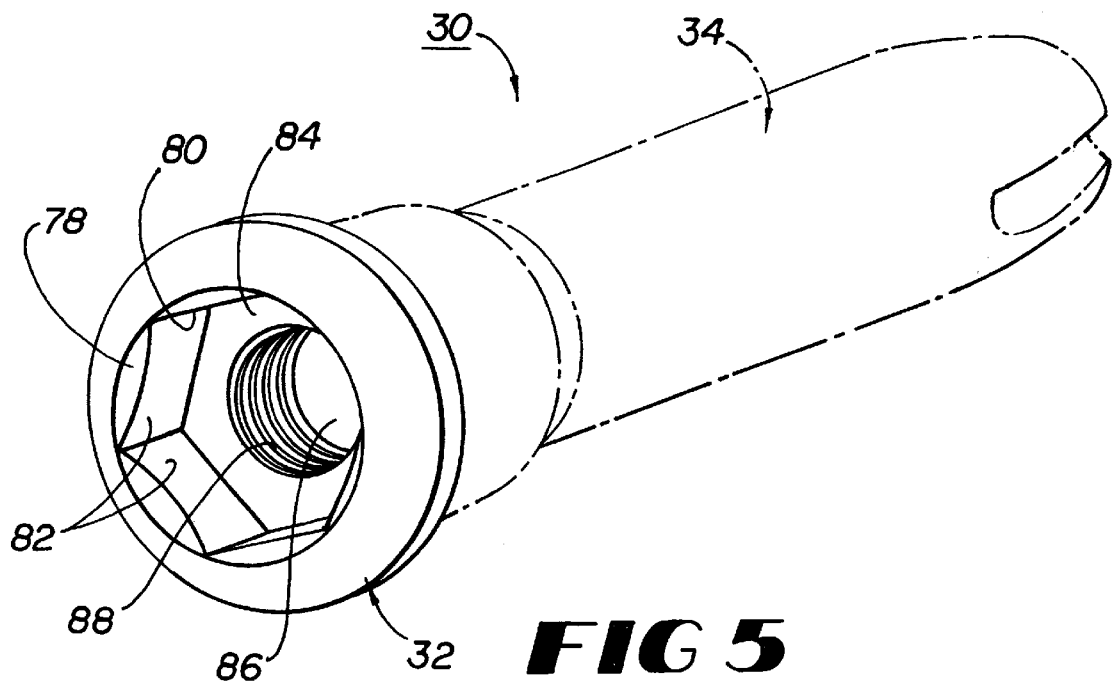
FIG. 5 is a perspective view of the head and internal capture surface of a screw according to one embodiment of this invention.
Figure 6:
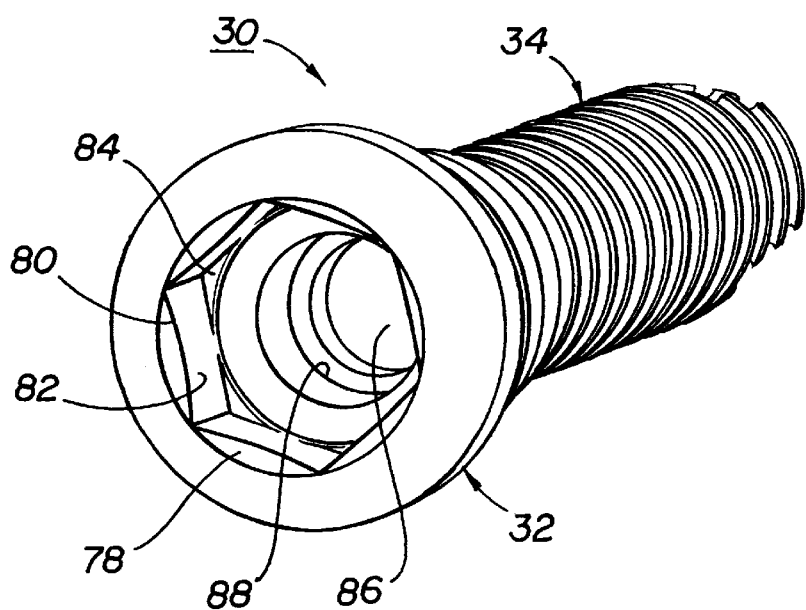
FIG. 6 is a perspective view of the head and internal capture surface of the screw of FIG. 1.

In the embodiment shown in FIGS. 4 through 6, screw thread 40, like the shank 38, varies along the length of the screw body 34 and is adapted to the needs and functions of the various regions of the screw. Although the pitch of thread 40 remains substantially constant, thread sections 72, 60, and 66 along corresponding shank sections 50, 52, and 54, respectively, are structurally and functionally distinct. Additionally, thread sections 72, 60, and 66 also define three corresponding major diameters: fist major diameter 73, second major diameter 61, and third major diameter 67.

Thread 60 in intermediate section 52 has a substantially constant thread height 64, due to the substantially constant second minor diameter 53 and second major diameter 61 of shank 36 in intermediate section 52. The major diameter of the thread is suited to the size of the screw and the intended function; preferably, the major diameter is from about 3.5 mm to about 6.0 mm, more preferably from about 4.5 mm to about 5.0 mm. Additionally, the ridge top 62 of intermediate thread section 60 is preferably relatively broad and wide as if the pointed end has been shaved off. This flat ridge top is appropriate for the soft trabecular region of the bone where the intermediate section 52 will reside. The flat ridge top and constant minor diameter of the intermediate section also suit a screw adapted for insertion through an aperture in an orthopedic implant for fixing the implant to the skeletal system of a patient.

Taper 58 on leading end 54 results in a decreasing minor diameter 55, but the third major diameter 67 is the same as second major diameter 61. The substantially constant major diameter through intermediate section 52 and leading end 54 results in a thread height 70 of thread 66 along leading end 54 that is greater than the thread height 64 of thread 60 in intermediate section 52. This increased thread height provides a better "bite" or grasp into the bone and more effectively draws the screw into the bone. The ridge top 68 in this section is narrow, or pointy, for better pull through and purchase, particularly on the far cortex of the bone. The cortex, unlike the trabecula, is hard and provides strength to the bone, and thus requires a stronger grasp.

In trailing end 50 the thread height 76 of thread 66 is also greater than thread height 64 of intermediate thread section 60 because both the first minor diameter 51 and first major diameter 73 increase along taper 56 in the direction of the screw head 32, providing room for the recessed internal capture surface, increased strength, and a tight wedge fit of the trailing end of the screw. The ridge top 74 of thread 72 along trailing end 50 is also generally narrow and pointy to provide for better seating of the screw and better purchase in the hard bone material of the near cortex.

The dual tapers 56, 58 and an increased height of thread 40 on leading end 54 and trailing end 50 of screw 30 provides improved purchase on both the near and far cortex of the bone. Intermediate section 52 does not require a tapered geometry or as high thread height because it occupies the inner portion of the bone with trabecular bone tissue, a softer, spongy bone tissue, and optionally occupies the interior of an aperture in an orthopedic implant when the screw is used for fixing an orthopedic implant in a patient.

As discussed above, the trailing end 50 of shank 36 has an enlarged minor diameter 51 to provide structural reinforcement for the internal capture surface, which is recessed into the head and optionally into at least part of the screw body 34. In one embodiment of the invention, the internal capture surface includes a recessed geometrically shaped socket adapted to engage a corresponding driver and an axial bore extending from the bottom of the socket into the upper portion of the screw shank. The bore includes connecting structure that corresponds to connecting structure on the driver. The connecting structure may be any suitable structure that couples the screw to the driver, such as threads, or a snap ring.

FIGS. 5 and 6 show one embodiment of head 32 with internal capture surface 78 of a screw according to this invention. Internal capture surface 78 is recessed into screw head 32 to allow the screw to be adequately seated and optionally countersunk into the bone while still being secured to a driver. Generally, a screw according to this invention will have an internal capture surface which includes both a driving surface and a connecting structure for securing the screw to a corresponding connecting structure on a driver in a manner that allows the screw to stay positioned on the driver during manipulation of the screw, yet be released when desired.

Internal capture surface 78 includes a female socket 80 that is recessed in screw head 32 and provides a driving surface. In this embodiment the socket 80 has a hexagonal shape with sides 82 and bottom 84. The socket according to the invention may be any geometric shape capable of bearing a torque load applied by a corresponding geometrically shaped driver. Possible shapes include, but are not limited, to hexagons, squares, other polygons, and ovals or other oblong shapes.

Figure 6A:
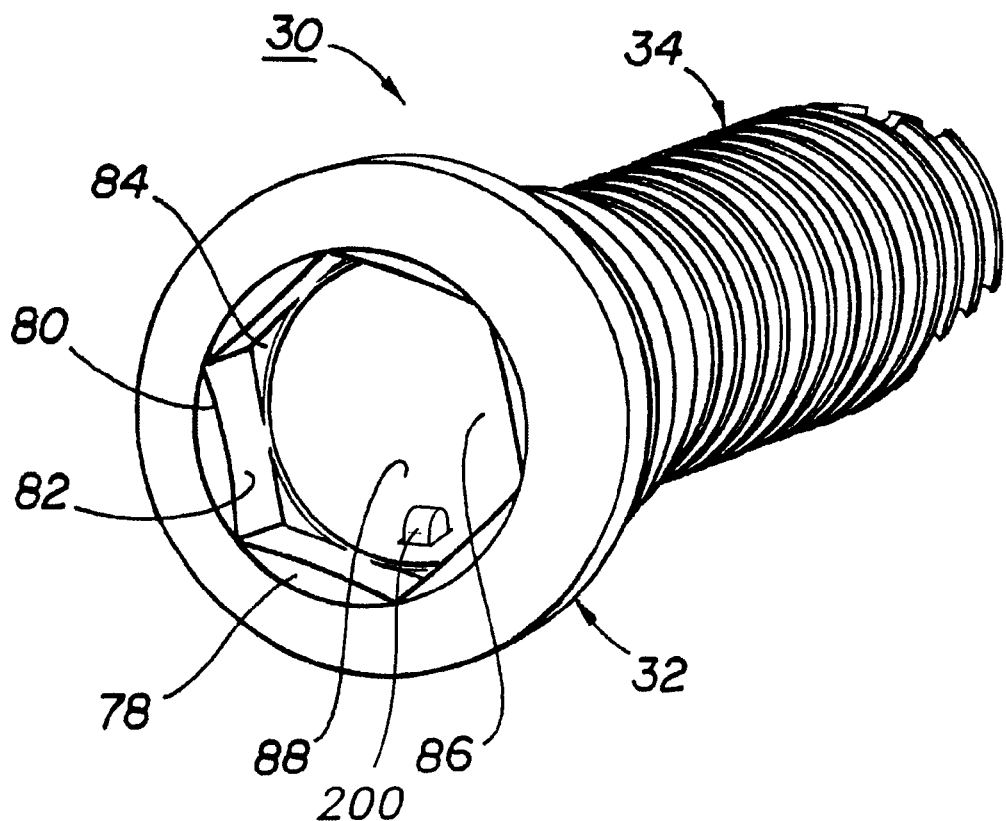
FIG. 6A is a perspective view of the head and internal capture surface of the screw according to another embodiment of the invention, having a ball plunger mechanism.
Figure 13:
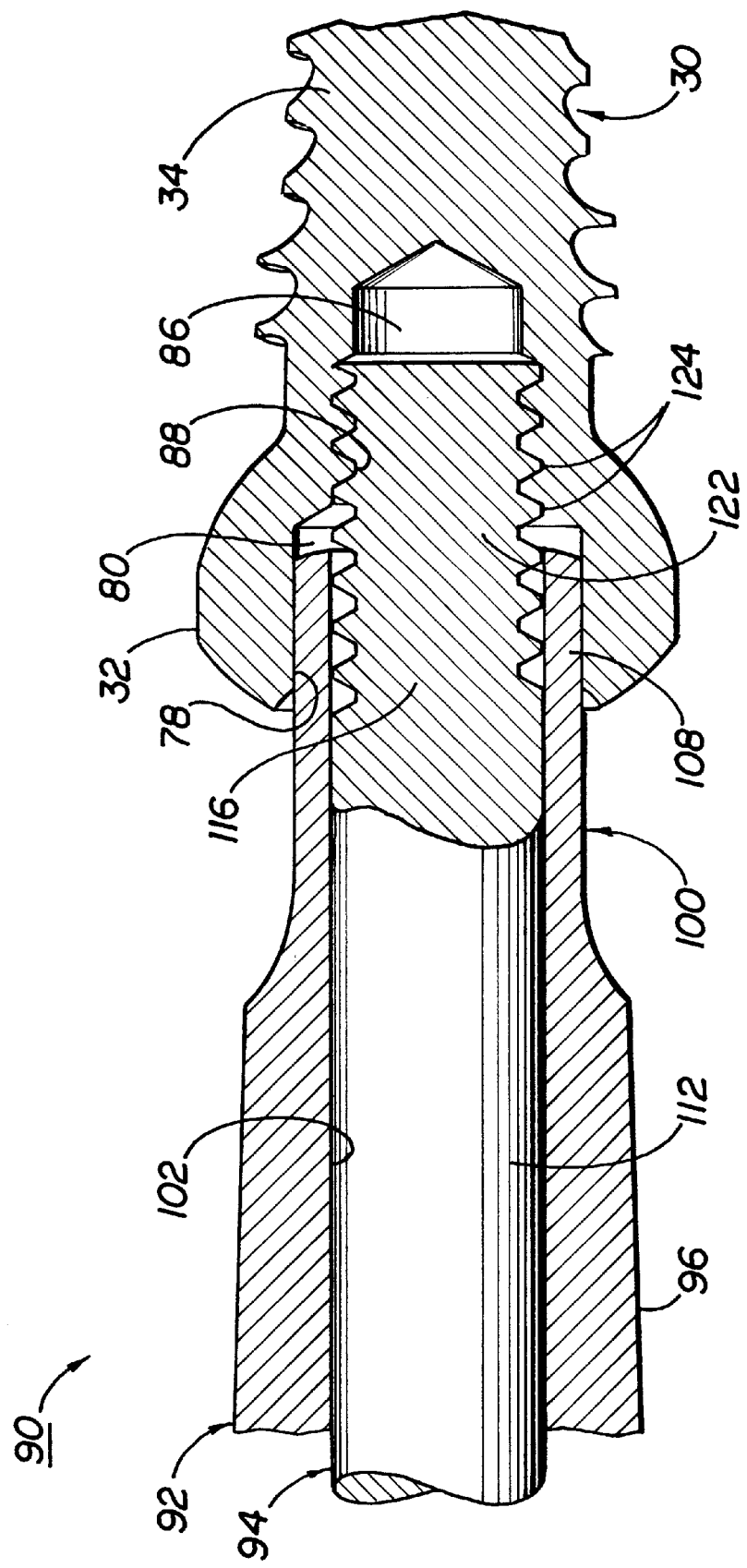
FIG. 13 is an exploded, cross-sectional view of a portion of a screw assembly according to one embodiment of this invention.

The screw according to the embodiment of the invention depicted in FIGS. 5 and 6 has a hex socket 80 with an axial bore 86 through the bottom 84 of the hex 80. In one embodiment, axial bore 86 includes internal threads 88 to engage corresponding external threads on a driver to secure the screw to a driver to avoid screw loss during insertion into a patient and to allow easy release of the screw after insertion. Alternative connecting structures may include a groove in the internal capture surface for accommodating a snap ring on a driver, or a small indentation in a side of the internal capture surface to correspond to a ball plunger device 200 on a driver, as shown in FIG. 6A.

A driver according to one embodiment of this invention is adapted to correspond to the internal capture surface of the screw head. FIGS. 7 through 9 depict a driver adapted to correspond to the internal capture surface 78 described in FIGS. 5 and 6. Driver 90 includes driving member 92 and retaining or locking member 94.

Driving member 92 includes a sleeve 96 with a first end 98, a second end 100, and a cannulation 102 therethrough. First end 98 includes a connector 104 adapted to engage a conventional driving device (e.g. a manual handle or power driver) and second end 100 includes a geometrically-shaped male end 106 adapted to engage the corresponding geometrically-shaped female socket 80 of screw head 32. In one embodiment, the geometrically shaped male end 106 of second end 100 is an external hex 108 adapted to engage internal hex socket 80 of screw head 32. External hex 108 has sides 110 corresponding to the sides 82 of hex socket 80. However, as discussed above, second end 100 may be any structure that corresponds to the shape of the internal socket of the screw head, which can be any shape capable of bearing a torque load. Thus, the geometrically shaped male end 106 may have other shapes such as oval, square, triangle, or other polygon.

Driver 90 also includes a retaining or locking member 94. In one embodiment, shown in FIG. 8, locking member 94 is elongated rod 112, insertable within cannulation 102 of sleeve 96. Rod 112 has a first end 114 and a second end 116. First end 114 may optionally include a tip 118 with a recess or slot 120 adapted to engage a driver such as a flathead or Phillips screwdriver. Second end 116 has structure that corresponds to connecting structure in screw head 32, so that rod 112 is inserted within the sleeve 96 and engages screw 30. In this manner, screw 30 is drawn toward and rests adjacent to assembled driver 90. In one embodiment of the invention, shown in FIGS. 5 and 6, axial bore 86 of head 32 has internal threads 88, and locking member 94 has externally threaded portion 122 with threads 124 on second end 116 adapted to engage the internal threads 88 of axial bore 86 of screw 30. Thus, in this embodiment, the connecting structure is a threaded bore and corresponding threaded rod, which provides a sufficiently rigid, but easily releasable internal capture surface. Alternative locking members include, but are not limited to snap rings and ball plunger devices. These and other capture mechanisms known to those of skill in the art are included within the scope of this invention.

FIG. 9 shows locking member 94 inserted within driving member 92 to form assembled driver 90. FIGS. 10 through 12 show exploded and assembled views of a screw and driver assembly according to this invention.

One method of using one form of structure according to this invention, which includes an orthopedic screw and driver for securing a rod or nail, is as follows. Driving member 92 of driver 90 is coupled with screw 30 by inserting the hex driver 108 of second end 100 of sleeve 96 into the hex socket 80 of internal capture surface 78 in screw head 32. With the driving member 92 inserted into the corresponding recessed socket of the screw head 32, locking member 94 is inserted through cannulation 102 of sleeve 96 of driving member 92 and engages the connecting structure of screw 30. In the embodiment described in the figures, external threads 124 of locking member 94 engage internal threads 88 of axial bore 86 in the screw 30, drawing the screw up securely against the external hex 108 of driving member 92 and rigidly securing screw 30 to the driver 90.

After screw 30 and driver 90 are securely assembled, screw 30 is inserted into a pre-drilled hole and advanced into the bone. If a screw according this invention is self drilling and self tapping, a pre-drilled hole is not necessary. When screw 30 is firmly seated in the bone, the surgeon may disengage driver 90 from screw 30 by separating locking member 94 from internal capture surface 78 of screw 30, removing locking member 94 from driving member 92 and removing driving member 92 from socket 80. In one embodiment, disengaging driver 90 involves unscrewing locking member 94 from internal threads 88 of screw 30.

A screw according to this invention may be used alone in the reduction of small bone fractures by placing the screw in the fracture to draw the bone fragments together for better healing. However, in many instances a screw of this invention will be used in a procedure for fixing an orthopedic implant in a patient by securing the implant to the skeletal system of a patient. The orthopedic implant used may be one adapted for use in the repair of bone fractures, such as an intramedullary nail, fracture reduction rod, orthopedic plate, or external fixture. Alternatively, the orthopedic implant may be adapted for replacement of a portion of a patient's skeletal system with a prosthesis; such implants include, but are not limited to acetabular shells and tibia bases.

One method of using a screw according to this invention in the fixation of an orthopedic implant involves providing an implant, such as an intramedullary nail, and surgically placing the implant in the patient. Once the implant is positioned as desired, the surgeon drills a hole in to the patient's bone, such that the hole is aligned with an aperture in the orthopedic implant, which is adapted to receive an orthopedic screw. The diameter of the pre-drilled hole should be less than that of the major diameter of the screw, such that the threads of the screw cut into the bone material. A screw according to this invention is then attached to a corresponding driver as described above and as shown in FIGS. 9 through 14. The surgeon then places the tip of the screw into the pre-drilled hole and applies torque to the driver to manipulate the screw into the bone and through the aperture in the orthopedic implant. Optionally, the leading end of the screw exits the opposite side of the implant aperture and contacts the far cortex of the bone. When the screw is positioned in the bone as desired, the surgeon then detaches the screw from the driver, as described above, leaving the screw securely seated in the bone and orthopedic implant, thereby securing the orthopedic implant to the patient's skeletal system.

Figure 14:
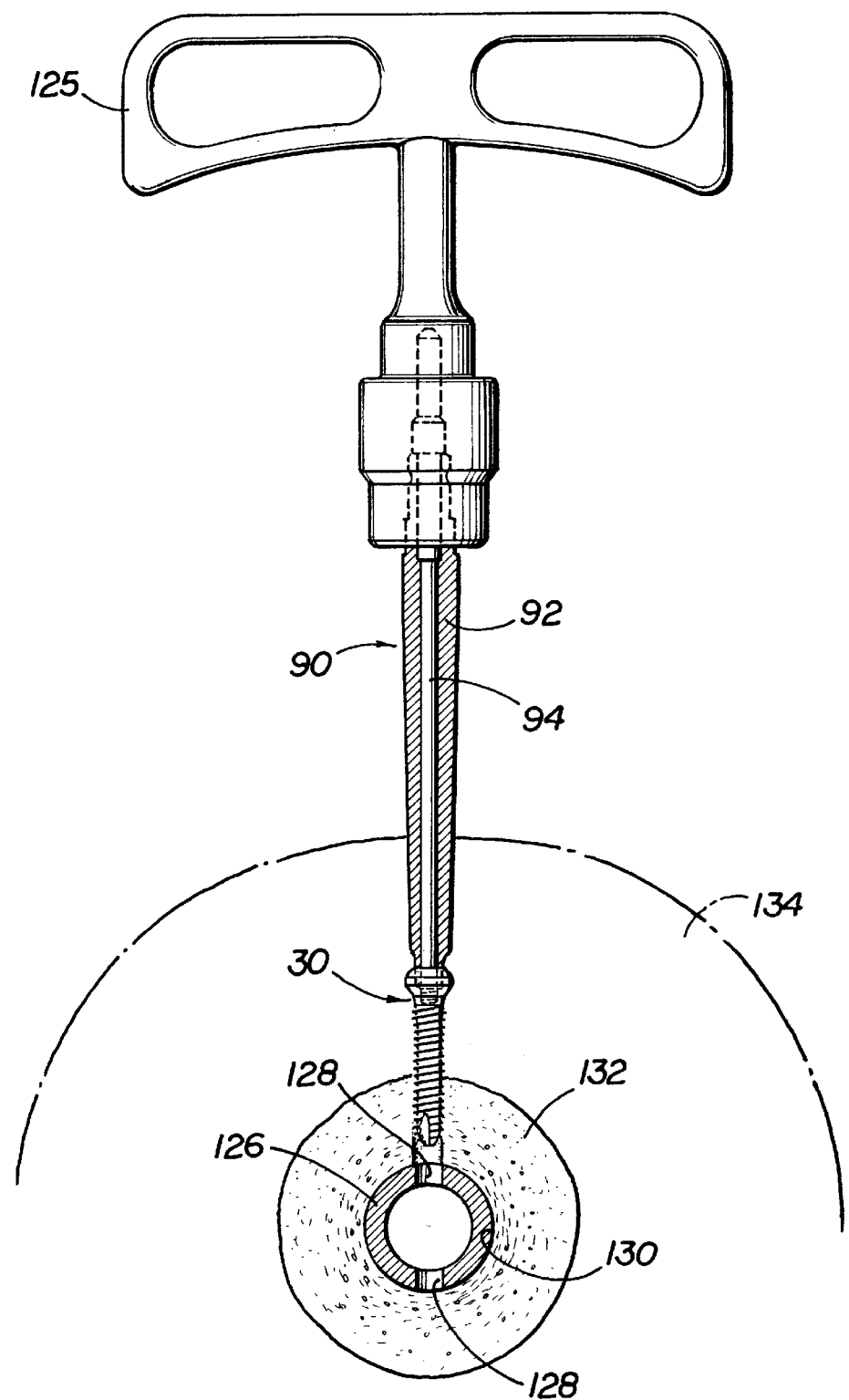
FIG. 14 is a side view in partial cross-section of a screw assembly according to one embodiment of this invention being used to implant a screw into a patient to secure an orthopedic implant.
Figure 15:
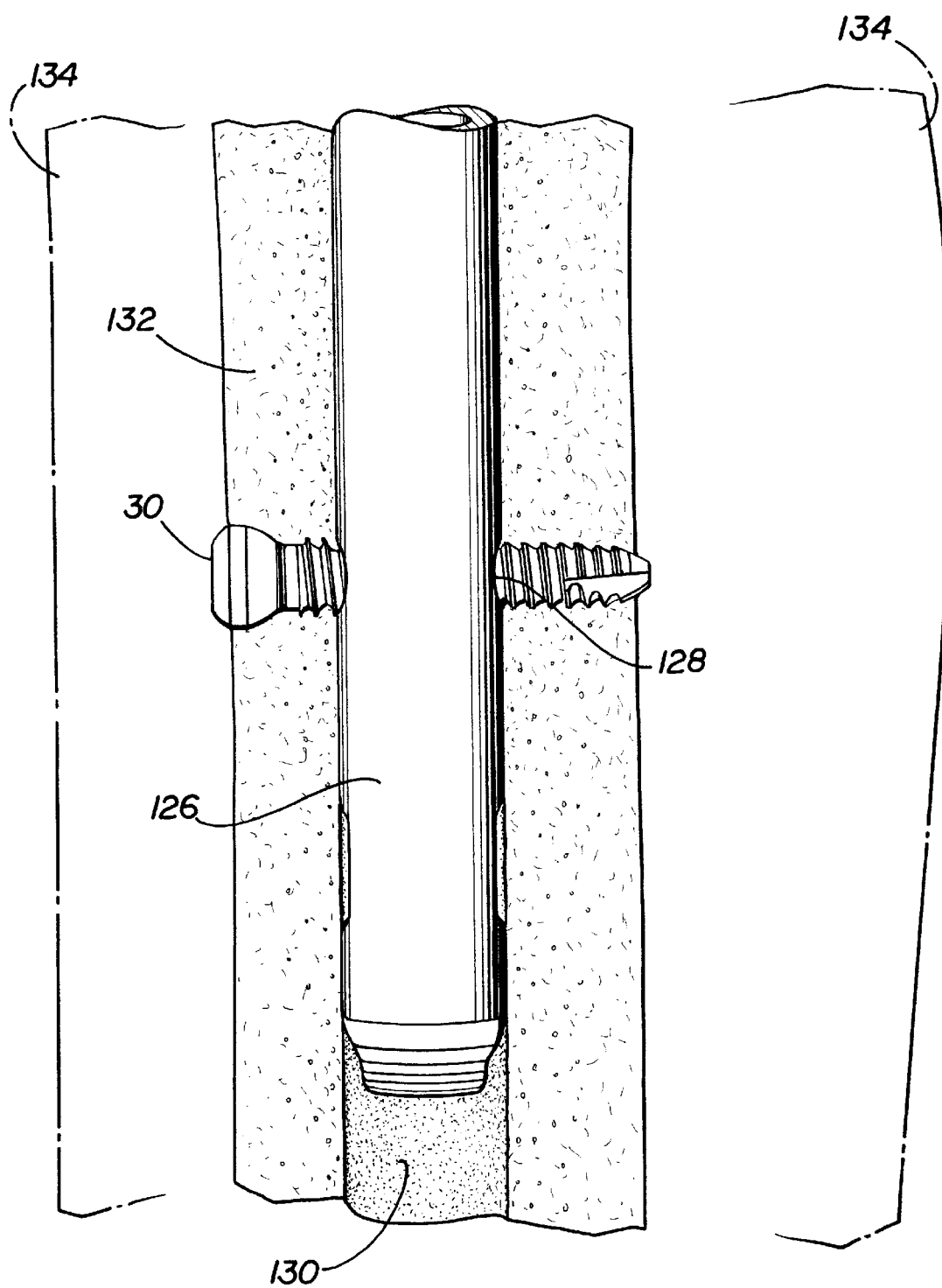
FIG. 15 is a perspective anatomical view of a screw according to one embodiment of this invention used to secure an intramedullary nail inserted in a bone of a patient.

FIG. 14 depicts a screw 30 and driver 90 according to this invention being used to insert screw 30 into a bone and through an aperture 128 in an intramedullary nail 126 in the bone of a patient. In this figure, a manual driving handle 125 has been attached to the connection configuration 104 on the first end of driving member 92 to allow the surgeon to manually apply torque to the driver 90, thereby rotating the screw to manipulate it into the bone material. FIG. 15 shows an anatomical perspective view of a system according to this invention including a screw 30 of this invention used to securely fix and provide rotational stability to an intramedullary nail 126 which has been placed in the intramedullary canal 130 of a patient's bone 132, shown surrounded by soft tissue 134. As shown, screw 30 is inserted through the cortical bone material 132 and through aperture 128 in the intramedullary nail 126, thereby securing and stabilizing nail 126.

The foregoing description of the, preferred embodiments of the invention has been presented only for the purpose of illustration and description and is not intended to be exhaustive or to limit the invention to the precise forms disclosed. Many modifications and variations are possible in light of the above teaching. The embodiments were chosen and described in order to explain the principles of the invention and their practical application so as to enable others skilled in the art to utilize the invention and various embodiments and with various modifications as are suited to the particular use contemplated.

What is claimed is:

1. An orthopedic screw for use in a surgical procedure comprising:
   (a) a head;
   (b) a body comprising:
      a distal tip;
      a shank extending from the head to the tip, the shank having a leading end adjacent the distal tip, a trailing end adjacent the head, and an intermediate section extending between the leading end and the trailing end,
         wherein the trailing end has a first diameter and the intermediate section has a second diameter, and
         wherein the first diameter is greater than the second diameter at least in part to accommodate an internal capture surface recessed into the head, the capture surface coaxial with the trailing end of the body; and
      a substantially continuous thread extending along at least a portion of the body, the thread extending radially outward from the shank; and
   (c) an internal capture surface recessed into the head and into at least a portion of the body, wherein the internal capture surface is adapted to receive a driver in order to secure the screw to the driver in a manner that allows the screw to stay positioned on the driver during manipulation of the screw, yet be released when desired,
      wherein the screw further comprises a major diameter defined by the substantially continuous thread,
      wherein the trailing end has a first major diameter and the intermediate section has a second major diameter,
      wherein the leading end has a third major diameter, and
      wherein the shank is tapered at the leading end, such that the third diameter decreases along the leading end in the direction of the distal tip, and the third major diameter remains substantially constant and is substantially equal to the second major diameter, such that the combination of the decreasing third shank diameter and constant third major diameter result in an increasing thread height of the thread along the leading end in the direction of the distal tip.

2. An orthopedic screw for use in a surgical procedure comprising:
   (a) a head;
   (b) a body comprising:
      a distal tip;
      a shank extending from the head to the tip, the shank having a leading end adjacent the distal tip, a trailing end adjacent the head, and an intermediate section extending between the leading end and the trailing end,
         wherein the trailing end has a first diameter and the intermediate section has a second diameter, and
         wherein the first diameter is greater than the second diameter at least in part to accommodate an internal capture surface recessed into the head, the capture surface coaxial with the trailing end of the body; and
      a substantially continuous thread extending along at least a portion of the body, the thread extending radially outward from the shank; and
   (c) an internal capture surface recessed into the head and into at least a portion of the body, wherein the internal capture surface is adapted to receive a driver in order to secure the screw to the driver in a manner that allows the screw to stay positioned on the driver during manipulation of the screw, yet be released when desired,
      wherein the internal capture surface comprises:
         a geometrically-shaped female socket adapted to receive a corresponding geometrically-shaped male end of a driver, and
         a connecting structure adapted to connect to a corresponding connecting structure on a locking member of a driver, and
            wherein the connecting structure comprises a generally circular groove adapted to function with a snap ring on a locking member of a driver, such that when the snap ring engages the groove the screw is secured to the driver in a manner that allows the screw to stay positioned on the driver during manipulation of the screw, yet be released when desired.

3. An orthopedic screw for use in a surgical procedure comprising:
   (a) a head;
   (b) a body comprising:
      a distal tip;
      a shank extending from the head to the tip, the shank having a leading end adjacent the distal tip, a trailing end adjacent the head, and an intermediate section extending between the leading end and the trailing end,
         wherein the trailing end has a first diameter and the intermediate section has a second diameter, and
         wherein the first diameter is greater than the second diameter at least in part to accommodate an internal capture surface recessed into the head, the capture surface coaxial with the trailing end of the body; and
      a substantially continuous thread extending along at least a portion of the body, the thread extending radially outward from the shank; and
   (c) an internal capture surface recessed into the head and into at least a portion of the body, wherein the internal capture surface is adapted to receive a driver in order to secure the screw to the driver in a manner that allows the screw to stay positioned on the driver during manipulation of the screw, yet be released when desired, wherein the internal capture surface comprises:
    a geometrically-shaped female socket adapted to receive a corresponding geometrically-shaped male end of a driver, and
    a connecting structure adapted to connect to a corresponding connecting structure on a locking member of a driver, and
        wherein the connecting structure comprises an indentation on an inside surface of the internal capture surface which is adapted to function with a ball plunger mechanism on a locking member of a driver, such that when the ball plunger engages the indentation, the screw is secured to the driver in a manner that allows the screw to stay positioned on the driver during manipulation of the screw, yet be released when desired.

4. A orthopedic screw for use in a surgical procedure comprising:
(a) a head;
(b) a body comprising:
    a generally conical distal tip;
    a shank extending from the head to the tip, the shank having a leading end adjacent the distal tip, a trailing end adjacent the head, and an intermediate section located between the leading end and trailing end,
        wherein the trailing end has a first diameter, the intermediate section has a second diameter and the leading end has a third diameter, and
        wherein the shank has a substantially cylindrical shape throughout the intermediate section and is tapered at both the leading and trailing ends such that the second diameter remains substantially constant along the intermediate section, the second diameter is greater than the third diameter, which decreases along the leading end in the direction of the conical tip, and the first diameter is greater than the second diameter and increases along the trailing end in the direction of the head, at least in part to accommodate an internal capture surface recessed into the head, the capture surface coaxial with the trailing end of the body; and
    a substantially continuous thread extending along at least a portion of the body, the thread extending radially outward from the shank and defining a first, second, and third major diameters, which are generally coaxial to first, second and third diameters of the shank, wherein the first major diameter is greater than the second major diameter, and the third major diameter is substantially equal to the second major diameter; and
(c) an internal capture surface recessed into the head and into at least a portion of the body, wherein the internal capture surface is adapted to receive a driver in order to secure the screw to the driver in a manner that allows the screw to stay positioned on the driver during manipulation of the screw, yet be released when desired.

5. A screw according to claim 4, wherein the internal capture surface comprises:
(a) a geometrically-shaped female socket adapted to receive a corresponding geometrically-shaped male end of a driver, and (b) a connecting structure adapted to connect to a corresponding connecting structure on a locking member of a driver.

6. A screw according to claim 5, where the geometrically-shaped female socket is in the shape of a polygon.

7. A screw according to claim 6, wherein the polygon is a hexagon.

8. A screw according to claim 6, wherein the polygon is a square.

9. A screw according to claim 5, wherein the geometrically shaped female socket is in the shape of an oval.

10. A screw according to claim 5, wherein the internal capture surface connecting structure comprises an axial bore extending through the bottom of the geometrically-shaped female socket and into at least a portion of the body, the bore further comprising internal threads around the circumference of the bore for engaging corresponding threads on a locking member of a driver.

11. A screw according to claim 5, wherein the connecting structure comprises a generally circular groove adapted to function with a snap ring on a locking member of a driver, such that when the snap ring engages the groove the screw is secured to the driver in a manner that allows the screw to stay positioned on the driver during manipulation of the screw, yet be released when desired.

12. A screw according to claim 5, wherein the connecting structure comprises an indentation on an inside surface of the internal capture surface which is adapted to function with a ball plunger mechanism on a locking member of a driver, such that when the ball plunger engages the indentation, the screw is secured to the driver in a manner that allows the screw to stay positioned on the driver during manipulation of the screw, yet be released when desired.

13. An orthopedic screw for use in a procedure for the fixation of an orthopedic implant in a patient comprising:
(a) a head adapted to countersink into a bone;
(b) a body comprising:
    a generally conical distal tip;
    a shank extending from the head to the tip, the shank having a leading end adjacent the distal tip, a trailing end adjacent the head, and an intermediate section located between the leading end and trailing end,
        wherein the trailing end has a first diameter, the intermediate section has a second diameter and the leading end has a third diameter, and
        wherein the shank has a substantially cylindrical shape throughout the intermediate section and is tapered at both the leading and trailing ends such that the second diameter remains substantially constant along the intermediate section, the second diameter is greater than the third diameter, which decreases along the leading end in the direction of the conical tip, and the first diameter is greater than the second diameter and increases along the trailing end in the direction of the head, at least in part to accommodate an internal capture surface recessed into the head, the capture surface coaxial with the trailing end of the body; and
    a substantially continuous thread extending along at least a portion of the body, the thread extending radially outward from the shank and defining a first, second, and third major diameters, which are generally coaxial to first, second and third diameters of the shank, wherein the first major diameter is greater than the second major diameter, and the third major diameter is substantially equal to the second major diameter; and (c) an internal capture surface recessed into the head and into at least a portion of the body, wherein the internal capture surface comprises:
a geometrically-shaped female socket adapted to receive a corresponding geometrically-shaped male end of a driver, and
an axial bore extending through the bottom of the geometrically-shaped socket and into at least a portion of the body, wherein the axial bore further comprises internal threads around the circumference of the bore for engaging corresponding threads on a locking member of a driver in order to secure the screw to the driver in a manner that allows the screw to stay positioned on the driver during manipulation of the screw, yet be released when desired.

14. A system for use in a procedure for the fixation of an orthopedic implant in a patient, comprising:
   (a) an orthopedic implant which is adapted to be implanted in a patient and held in place by one or more orthopedic screws, wherein the orthopedic implant comprises one or more apertures adapted to receive an orthopedic screw for securing the implant to the skeletal system of the patient as desired;
   (b) an orthopedic screw adapted for insertion into a bone and through an aperture in an orthopedic implant to secure the orthopedic implant to the skeletal system of the patient as desired, wherein the screw comprises:
      (i) a head;
      (ii) a body comprising:
         a distal tip;
         a shank extending from the head to the tip, the shank having a leading end adjacent the distal tip, a trailing end adjacent the head, and an intermediate section extending between the leading end and the trailing end,
            wherein the trailing end has a first diameter and the intermediate section has a second diameter, and
            wherein the first diameter is greater than the second diameter at least in part to accommodate an internal capture surface recessed into the head, the capture surface coaxial with the trailing end of the body; and
         a substantially continuous thread extending along at least a portion of the body, the thread extending radially outward from the shank; and
      (iii) an internal capture surface recessed into the head and into at least a portion of the body, wherein the internal capture surface is adapted to receive a driver in order to secure the screw to the driver in a manner that allows the screw to stay positioned on the driver during manipulation of the screw, yet be released when desired, and
         wherein the shank is tapered at the trailing end, such that the first diameter increases along the trailing end in the direction of the head.

15. A system for use in a procedure for the fixation of an orthopedic implant in a patient, comprising:
   (a) an orthopedic implant which is adapted to be implanted in a patient and held in place by one or more orthopedic screws, wherein the orthopedic implant comprises one or more apertures adapted to receive an orthopedic screw for securing the implant to the skeletal system of the patient as desired;
   (b) an orthopedic screw adapted for insertion into a bone and through an aperture in an orthopedic implant to secure the orthopedic implant to the skeletal system of the patient as desired, wherein the screw comprises:
      (i) a head;
      (ii) a body comprising:
         a distal tip;
         a shank extending from the head to the tip, the shank having a leading end adjacent the distal tip, a trailing end adjacent the head, and an intermediate section extending between the leading end and the trailing end,
            wherein the trailing end has a first diameter and the intermediate section has a second diameter, and
            wherein the first diameter is greater than the second diameter at least in part to accommodate an internal capture surface recessed into the head, the capture surface coaxial with the trailing end of the body; and
         a substantially continuous thread extending along at least a portion of the body, the thread extending radially outward from the shank; and
      (iii) an internal capture surface recessed into the head and into at least a portion of the body, wherein the internal capture surface is adapted to receive a driver in order to secure the screw to the driver in a manner that allows the screw to stay positioned on the driver during manipulation of the screw, yet be released when desired,
   wherein the screw further comprises a major diameter defined by the substantially continuous thread, and wherein the trailing end has a first major diameter and the intermediate section has a second major diameter, wherein the leading end has a third major diameter, and
   wherein the shank is tapered at the leading end, such that the third diameter decreases along the leading end in the direction of the distal tip, and the third major diameter remains substantially constant and is substantially equal to the second major diameter, such that the combination of the decreasing third shank diameter and constant third major diameter result in an increasing thread height of the thread along the leading end in the direction of the distal tip.

16. A system for use in a procedure for the fixation of an orthopedic implant in a patient, comprising:
   (a) an orthopedic implant which is adapted to be implanted in a patient and held in place by one or more orthopedic screws, wherein the orthopedic implant comprises one or more apertures adapted to receive an orthopedic screw for securing the implant to the skeletal system of the patient as desired;
   (b) an orthopedic screw adapted for insertion into a bone and through an aperture in an orthopedic implant to secure the orthopedic implant to the skeletal system of the patient as desired, wherein the screw comprises:
      (i) a head;
      (ii) a body comprising:
         a distal tip;
         a shank extending from the head to the tip, the shank having a leading end adjacent the distal tip, a trailing end adjacent the head, and an intermediate section extending between the leading end and the trailing end,
            wherein the trailing end has a first diameter and the intermediate section has a second diameter, and
            wherein the first diameter is greater than the second diameter at least in part to accommodate an internal capture surface recessed into the head, the capture surface coaxial with the trailing end of the body; and a substantially continuous thread extending along at least a portion, of the body, the thread extending radially outward from the shank; and (iii) an internal capture surface recessed into the head and into at least a portion of the body, wherein the internal capture surface is adapted to receive a driver in order to secure the screw to the driver in a manner that allows the screw to stay positioned on the driver during manipulation of the screw, yet be released when desired, further comprising a driver for manipulating the screw into the bone and through an aperture in the orthopedic implant, wherein the driver comprises:

(a) a driving member comprising a first end adapted to engage a conventional driving device and a second end adapted to be received within the internal capture surface of the screw and to engage the screw; and (b) a locking member adapted to secure the screw to the driving member in a manner that allows the screw to stay positioned on the driver during manipulation of the screw, yet be released when desired.

17. A system for use in a procedure for the fixation of an orthopedic implant in a patient, comprising:

(a) an orthopedic implant which is adapted to be implanted in a patient and held in place by one or more orthopedic screws, wherein the orthopedic implant comprises one or more apertures adapted to receive an orthopedic screw for securing the implant to the skeletal system of the patient as desired;

(b) an orthopedic screw adapted for insertion into a bone and through an aperture in an orthopedic implant to secure the orthopedic implant to the skeletal system of the patient as desired, wherein the screw comprises:
  (i) a head;
  (ii) a body comprising:
    a distal tip;
    a shank extending from the head to the tip, the shank having a leading end adjacent the distal tip, a trailing end adjacent the head, and an intermediate section extending between the leading end and the trailing end,
      wherein the trailing end has a first diameter and the intermediate section has a second diameter, and
      wherein the first diameter is greater than the second diameter at least in part to accommodate an internal capture surface recessed into the head, the capture surface coaxial with the trailing end of the body; and
    a substantially continuous thread extending along at least a portion of the body, the thread extending radially outward from the shank; and
  (iii) an internal capture surface recessed into the head and into at least a portion of the body, wherein the internal capture surface is adapted to receive a driver in order to secure the screw to the driver in a manner that allows the screw to stay positioned on the driver during manipulation of the screw, yet be released when desired, wherein the internal capture surface of the screw comprises:
  (a) a geometrically-shaped female socket adapted to receive a corresponding geometrically-shaped male end of a driver, and
  (b) a connecting structure adapted to connect to a corresponding connecting structure on a locking member of a driver, wherein the connecting structure comprises an axial bore extending through the bottom of the geometrically-shaped socket and into at least a portion of the body, wherein the axial bore further comprises internal threads around the circumference of the bore for engaging corresponding threads on a locking member of a driver in order to secure the screw to the driver in a manner that allows the screw to stay positioned on the driver during manipulation of the screw, yet be released when desired, and further comprising a driver adapted to correspond to the internal capture surface of the screw and for manipulating the screw into the bone and through an aperture in the orthopedic implant comprising:

(a) a sleeve having a first end, a second end, and a cannulation therethrough,
  wherein the first end is adapted to engage a conventional driving device, and the second end comprises a geometrically-shaped male end adapted to correspond to the geometrically shaped female socket of the internal capture surface of the screw and to engage the screw; and (b) an elongated rod having a first end and a second end, wherein the rod is adapted to be inserted within the cannulation of the sleeve, and
  wherein the first end is adapted to engage a conventional driving device and the second end comprises external threads adapted to correspond to the internal threads of the axial bore of the screw to secure the screw to the driver, such that when the rod is inserted into the sleeve of the driving member and screwed into the axial bore the internal socket of the screw is drawn securely against the driving member, allowing the screw to stay positioned on the driver during manipulation of the screw, yet be released when desired.

18. A system for use in a procedure for the fracture reduction of bones, comprising:

(a) an intramedullary nail adapted to be inserted into an intramedullary canal of a long bone to stabilize a fracture of the bone, wherein the intramedullary nail comprises one or more apertures therethrough adapted to receive an orthopedic screw;

(b) an orthopedic screw adapted for insertion into the bone and through an aperture in the intramedullary nail, wherein the screw comprises:
  (i) a head;
  (ii) a body comprising:
    a generally conical distal tip;
    a shank extending from the head to the tip, the shank having a leading end adjacent the distal tip, a trailing end adjacent the head, and an intermediate section located between the leading end and trailing end,
      wherein the trailing end has a first diameter, the intermediate section has a second diameter and the leading end has a third diameter, and
      wherein the shank has a substantially cylindrical shape throughout the intermediate section and is tapered at both the leading and trailing ends such that the second diameter remains substantially constant along the intermediate section, the second diameter is greater than the third diameter, which decreases along the leading end in the direction of the conical tip, and the first diameter is greater than the second diameter and increases along the trailing end in the direction of the head, at least in part to accommodate an internal capture surface recessed into the head, the capture surface coaxial with the trailing end of the body; and a substantially continuous thread extending along at least a portion of the body, the thread extending radially outward from the shank and defining a first, second, and third major diameters, which are generally coaxial to first, second and third diameters of the shank, and wherein the first major diameter is greater than the second major diameter, and the third major diameter is substantially equal to the second major diameter; and (iii) an internal capture surface recessed into the head and into at least a portion of the body, wherein the internal capture surface is adapted to receive a driver, secure the screw to the driver in a manner that allows the screw to stay positioned on the driver during manipulation of the screw, yet be released when desired.

19. A system, according to claim 18, further comprising a driver for manipulating the screw into the bone and through an aperture in the intramedullary nail, wherein the driver comprises:

(a) a driving member comprising a first end adapted to engage a conventional driving device and a second end adapted to be received within the internal capture surface of the screw and to engage the screw; and (b) a locking member adapted to secure the screw to the driving member in a manner that allows the screw to stay positioned on the driver during manipulation of the screw, yet be released when desired.

20. A system according to claim 18, wherein the internal capture surface of the screw comprises:

(a) a geometrically-shaped female socket adapted to receive a corresponding geometrically-shaped male end of a driver, and (b) a connecting structure adapted to connect to a corresponding connecting structure on a locking member of a driver.

21. A system according to claim 20, wherein the connecting structure comprises an axial bore extending through the bottom of the geometrically-shaped socket and into at least a portion of the body, wherein the axial bore further comprises internal threads around the circumference of the bore for engaging corresponding threads on a locking member of a driver in order to secure the screw to the driver in a manner that allows the screw to stay positioned on the driver during manipulation of the screw, yet be released when desired.

22. The system according to claim 21, further comprising a driver for manipulating the screw into the bone and through an aperture in the intramedullary nail, wherein the driver comprises:

(a) a sleeve having a first end, a second end, and a cannulation therethrough, wherein the first end is adapted to engage a conventional driving device, and the second end comprises a geometrically-shaped male end adapted to correspond to the geometrically shaped female socket of the internal capture surface of the screw and to engage the screw; and (b) an elongated rod having a first end and a second end, wherein the rod is adapted to be inserted within the cannulation of the sleeve, and wherein the first end is adapted to engage a conventional driving device and the second end comprises external threads adapted to correspond to the internal threads of the axial bore of the screw to secure the screw to the driver, such that when the rod is inserted into the sleeve of the driving member and screwed into the axial bore the internal socket of the screw is drawn securely against the driving member, allowing the screw to stay positioned on the driver during manipulation of the screw, yet be released when desired.

23. A method of fixing an orthopedic implant in a patient comprising:

(a) providing an orthopedic implant which is adapted to be implanted in a patient and held in place by one or more orthopedic screws, wherein the orthopedic implant comprises one or more apertures adapted to receive an orthopedic screw for securing the implant to the patient's skeletal system as desired;

(b) providing an orthopedic screw an orthopedic screw adapted for insertion into a bone and through an aperture in an orthopedic implant to secure the orthopedic implant to the patient's skeletal system as desired, wherein the screw comprises:

(i) a head;
(ii) a body comprising:
a distal tip;
a shank extending from the head to the tip, the shank having a leading end adjacent the distal tip, a trailing end adjacent the head, and an intermediate section extending between the leading end and the trailing end,
wherein the trailing end has a first diameter and the intermediate section has a second diameter, and
wherein the first diameter is greater than the second diameter at least in part to accommodate an internal capture surface recessed into the head, the capture surface coaxial with the trailing end of the body; and
a substantially continuous thread extending along at least a portion of the body, the thread extending radially outward from the shank; and (iii) an internal capture surface recessed into the head and into at least a portion of the body, wherein the internal capture surface is adapted to receive a driver in order to rigidly secure the screw to the driver in a manner that allows the screw to stay positioned on the driver during manipulation of the screw, yet be released when desired;

(c) providing a driver comprising
(i) a driving member comprising a first end adapted to engage a conventional driving device and a second end adapted to be received within the internal capture surface of the screw and to engage the screw; and
(ii) a locking member adapted to secure the screw to the driving member in a manner that allows the screw to stay positioned on the driver during manipulation of the screw, yet be released when desired (d) implanting the orthopedic implant in a patient;
(e) drilling a hole in the bone which is aligned with an aperture of the orthopedic implant;
(f) inserting the second end of the driving member into the internal capture surface in the head of the screw;
(g) inserting the locking member into the internal capture surface in the head of the screw;
(h) coupling the locking member and screw by in a manner that draws the screw securely against the driving member, such that a rigid connection is maintained between the screw and driver during manipulation of the screw, yet allows release of the screw when desired;

(i) attaching a conventional driving device to the second end of the driver;
(j) inserting the tip of the screw into the pre-drilled hole in the bone;
(k) applying torque to the driving device to manipulate the screw into the bone and through the aperture in the orthopedic implant;
(l) securely seating the screw in the bone;
(m) disengaging the connecting configuration of the locking member and screw;
(n) removing the locking member from the internal capture surface of the screw; and
(o) removing the driving member from the internal capture surface to release the screw.

24. A method of repairing a bone fracture comprising:
(a) providing an intramedullary nail adapted to be inserted into an intramedullary canal of a long bone to stabilize a fracture of the bone,
   wherein the intramedullary nail comprises one or more apertures therethrough adapted to receive an orthopedic screw;
(b) providing an orthopedic screw adapted for insertion into the bone and through an aperture in the intramedullary nail, wherein the screw comprises:
   (i) a head;
   (ii) a body comprising:
      a generally conical distal tip;
      a shank extending from the head to the tip, the shank having a leading end adjacent the distal tip, a trailing end adjacent the head, and an intermediate section located between the leading end and trailing end,
         wherein the trailing end has a first diameter, the intermediate section has a second diameter and the leading end has a third diameter, and
         wherein the shank has a substantially cylindrical shape throughout the intermediate section and is tapered at both the leading and trailing ends such that the second diameter remains substantially constant along the intermediate section, the second diameter is greater than the third diameter, which decreases along the leading end in the direction of the conical tip, and the first diameter is greater than the second diameter and increases along the trailing end in the direction of the head, at least in part to accommodate an internal capture surface recessed into the head, the capture surface coaxial with the trailing end of the body; and
      a substantially continuous thread extending along at least a portion of the body, the thread extending radially outward from the shank and defining a first, second, and third major diametes, which are generally coaxial to first, second and third diameters of the shank, and wherein the first major diameter is greater than the second major diameter, and the third major diameter is substantially equal to the second major diameter; and
   (iii) an internal capture surface recessed into the head and into at least a portion of the body, wherein the internal capture surface of the screw comprises:
      a geometrically-shaped female socket adapted to receive a corresponding geometrically-shaped male end of a driver, and
      an axial bore extending through the bottom of the geometrically-shaped socket and into at least a portion of the body, wherein the axial bore further comprises internal threads around the circumference of the bore for engaging corresponding threads on a locking member of a driver in order to secure the screw to the driver in a manner that allows the screw to stay positioned on the driver during manipulation of the screw, yet be released when desired;
(c) providing a driver for manipulating the screw into the bone and through an aperture in the intramedullary nail, wherein the driver comprises:
   (i) a sleeve having a first end, a second end, and a cannulation therethrough,
      wherein the first end is adapted to engage a conventional driving device, and the second end comprises a geometrically-shaped male end adapted to correspond to the geometrically shaped female socket of the internal capture surface of the screw and to engage the screw; and
   (ii) an elongated rod having a first end and a second end, wherein the rod is adapted to be inserted within the cannulation of the sleeve, and
      wherein the first end is adapted to engage a conventional driving device and the second end comprises external threads adapted to correspond to the internal threads of the axial bore of the screw to secure the screw to the driver, such that when the rod is inserted into the sleeve of the driving member and screwed into the axial bore the internal socket of the screw is drawn securely against the driving member, allowing the screw to stay positioned on the driver during manipulation of the screw, yet be released when desired;
(d) implanting the intramedullary nail in the intramedullary canal of the long bone of a patient;
(e) drilling a hole in the bone which is aligned with an aperture of the orthopedic implant;
(f) inserting the geometrically-shaped male end of the driving member into the corresponding geometrically-shaped female socket of the internal capture surface in the head of the screw;
(g) inserting the locking member into the cannulation of the sleeve of driving member such that the second end of the elongated rod is inserted into the axial bore of the screw;
(h) rotating the locking member such that external threads on the second end of the locking member engage the corresponding internal threads of the axial bore of the screw, drawing the screw securely against the driving member, such that a rigid connection is maintained between the screw and driver;
(i) attaching a conventional driving device to the second end of the driver;
(j) inserting the tip of the screw into the pre-drilled hole in the bone;
(k) applying torque to the driving device to manipulate the screw into the bone;
(l) securely seating the screw in the bone;
(m) unscrewing the locking member to disengage the threaded end of the locking member from the corresponding threads of the axial bore of the screw;
(n) removing the locking member from the sleeve of the driving member; and
(o) removing the driving member from the internal socket of the head to release the screw.

* * * * *